US007803872B2

(12) United States Patent
Verrall et al.

(10) Patent No.: US 7,803,872 B2
(45) Date of Patent: Sep. 28, 2010

(54) HALOGEN-RESISTANT COMPOSITION

(75) Inventors: Andrew P. Verrall, Crown Point, IN (US); Stephen D. Goodrich, St. John, IN (US)

(73) Assignee: Monosol, LLC, Merrillville, IN (US)

( * ) Notice: Subject to any disclaimer, the term of this patent is extended or adjusted under 35 U.S.C. 154(b) by 444 days.

(21) Appl. No.: 11/739,473

(22) Filed: Apr. 24, 2007

(65) Prior Publication Data

US 2007/0254017 A1 Nov. 1, 2007

Related U.S. Application Data

(60) Provisional application No. 60/796,378, filed on May 1, 2006.

(51) Int. Cl.
*C08F 8/00* (2006.01)

(52) U.S. Cl. .................... 525/61; 428/500; 524/57; 524/377; 524/557; 525/57; 525/340; 525/343; 525/348; 525/374; 525/380; 525/383

(58) Field of Classification Search .................. 524/57, 524/377, 557; 525/57, 61, 340, 343, 348, 525/374, 380, 383; 428/500
See application file for complete search history.

(56) References Cited

U.S. PATENT DOCUMENTS

| 5,258,422 | A | 11/1993 | Chang et al. |
| 5,851,406 | A | 12/1998 | Jones et al. |
| 6,166,117 | A | 12/2000 | Miyazaki |
| 6,608,121 | B2 | 8/2003 | Isozaki et al. |
| 6,818,709 | B1 | 11/2004 | Vicari |
| 6,898,921 | B2 | 5/2005 | Duffield |
| 7,022,656 | B2 | 4/2006 | Verrall et al. |
| 7,115,173 | B2 * | 10/2006 | Caswell et al. ................ 134/42 |
| 2002/0182348 | A1 | 12/2002 | Fujiwara et al. |
| 2003/0104969 | A1 | 6/2003 | Caswell et al. |
| 2004/0002433 | A1 | 1/2004 | Buckland et al. |
| 2004/0186034 | A1 | 9/2004 | Verrall et al. |
| 2005/0048234 | A1 | 3/2005 | Duffield |
| 2005/0154120 | A1 | 7/2005 | Echt et al. |
| 2005/0222355 | A1 | 10/2005 | Vicari |
| 2006/0008605 | A1 | 1/2006 | Boswell et al. |
| 2006/0035042 | A1 | 2/2006 | Morken |
| 2006/0281839 | A1 | 12/2006 | Barthel et al. |
| 2009/0054295 | A1 | 2/2009 | Vicari et al. |

FOREIGN PATENT DOCUMENTS

| EP | 0 884 352 A1 | 12/1998 |
| EP | 1 251 147 A1 | 10/2002 |
| EP | 2 031 049 A2 | 3/2009 |
| WO | WO 2005/051770 A1 | 6/2005 |

OTHER PUBLICATIONS

International Search Report and Written Opinion of the International Searching Authority for counterpart PCT Application No. PCT/US2007/067311, mailed Sep. 13, 2007.

* cited by examiner

*Primary Examiner*—David Wu
*Assistant Examiner*—Marie Reddick
(74) *Attorney, Agent, or Firm*—Marshall, Gerstein & Borun LLP

(57) ABSTRACT

A water-soluble, halogen-resistant film-forming composition useful for packaging water treatment products is disclosed. The film can include an acid-stable, water-soluble polyvinyl alcohol polymer, an oxidizable organic material, a chelating agent, a free radical scavenger, and secondary additives such as plasticizers, lubricants, and surfactants. The resulting film has favorable solubility properties after having been exposed to halogenated (e.g., chlorinated and brominated) compositions such as water treatment and agricultural products for prolonged periods of time.

25 Claims, 2 Drawing Sheets

HALOGEN-RESISTANT COMPOSITION

CROSS REFERENCE TO RELATED APPLICATIONS

The benefit under 35 USC §119(e) of U.S. provisional patent application Ser. No. 60/796,378, filed May 1, 2006, the disclosure of which is incorporated herein by reference, is claimed.

BACKGROUND

1. Field of the Disclosure

The disclosure relates to a halogen-resistant film-forming composition which can be used for packaging products containing reactive halogenated compounds, such as chlorinated or brominated water treatment products. More particularly, the disclosure relates to a halogen-resistant film including an acid-stable, water-soluble polyvinyl alcohol polymer, an oxidizable organic material, a chelating agent, and a free radical scavenger.

2. Brief Description of Related Technology

One of the many applications of the unit dose packaging concept employing water-soluble films is the packaging of water treatment products, in particular those that contain available chlorine and bromine. This configuration facilitates water treatment processes by allowing the contained chemical (including the packaging film) to be incorporated into the process without the need for opening and disposing of the packaging film. For example, a film package containing a swimming pool sanitizing chemical may be added directly to the pool water in the pool's water treatment system.

While the use of water-soluble films is convenient in applications using these types of reactive halogenated chemicals, prior water-soluble films exhibit compatibility limitations when placed in contact with them. For example, contact with chlorinated and brominated chemicals containing available chlorine and bromine for as little as a week can discolor a non-resistant film and impair its solubility characteristics. Specifically, the films may become soluble in hot water only (i.e., as opposed to being soluble in hot and cold water), or may even become altogether insoluble in water.

SUMMARY

One aspect of the disclosure provides a halogen-resistant, water-soluble film-forming composition including an acid-stable, water-soluble polyvinyl alcohol ("PVOH") polymer, an oxidizable organic material, a chelating agent, and a free radical scavenger.

Another aspect of the disclosure provides a halogen-resistant, water-soluble film including a mixture of an acid-stable, water-soluble polyvinyl alcohol polymer and an additive selected from the group consisting of an oxidizable organic material, a chelating agent, a free radical scavenger, and combinations thereof; wherein a 50 μm sample of the water-soluble film stored in contact with a halogenated composition including 56 wt. % sodium dichloroisocyanurate as the active ingredient for 28 days at 38° C. and 85% relative humidity is characterized by an increase in dissolution time of not more than 15%, when measured in water at 10° C.

Another aspect of the disclosure provides a halogen-resistant film-forming composition, including a mixture of an acid-stable, water-soluble polymer comprising polyvinyl alcohol containing a stabilizing functional group selected from the group consisting of sulfonic acid, including its alkali metal salts; carboxylic acid, including its alkali metal salts; amine; amide; cationic nitrogen; and combinations thereof; an oxidizable organic material selected from the group consisting of polyethylene glycol, methoxypolyethylene glycol, polypropylene glycol, any reducing sugars such as glucose, fructose, maltose and glyceraldehyde, and combinations thereof; a chelating agent selected from the group consisting of phosphonic acids, phosphonates, polyphosphates, polyaminocarboxylic acids, and combinations thereof; and, a free radical scavenger selected from the group consisting of 4-methoxy phenol, hydroquinone, ascorbic acid, butylated hydroxyanisole, mercaptopropionic acid, N-acetylcysteine, dimethylthiourea, pyrrolidine dithiocarbamate, hydroxylamines, monoterpene ketones, and combinations thereof; wherein the halogen-resistant composition is optionally in the form of a water-soluble film optionally formed into a package.

Another aspect of the disclosure provides a pre-packaged article including a reactive halogenated component contained in a water-soluble film package formed from a halogen-resistant film disclosed herein.

Further aspects and advantages will be apparent to those of ordinary skill in the art from a review of the following detailed description. While the compositions and articles are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

Objects, features, and advantages of the present disclosure will become apparent upon reading the following description in conjunction with the drawing figures, in which.

DETAILED DESCRIPTION

Figure 3:
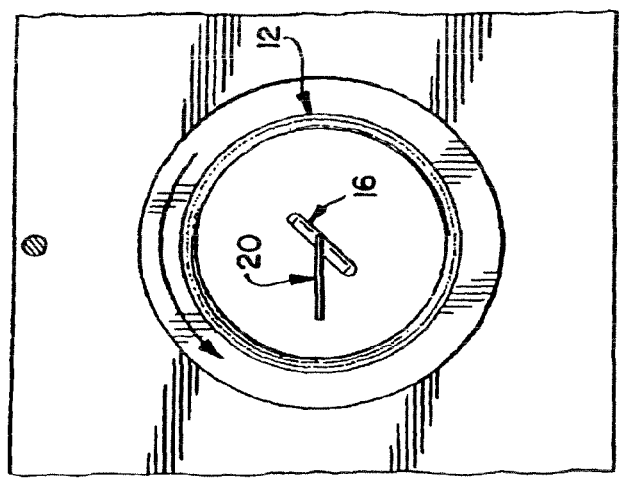

As used herein, the components and characteristics of a "halogen-resistant film-forming composition" can apply to both the composition itself and a film formed from the composition, unless specified otherwise. The compositions generally comprise an acid-stable, water-soluble polymer, an oxidizable organic material, a chelating agent, and a free radical scavenger. The resulting films have advantageous water solubility characteristics after prolonged exposure to reactive halogenated compounds. Preferably, the halogen-resistant film-forming composition is soluble in cold water (e.g., about 5° C. to about 30° C., for example about 10° C.).

Unless specified otherwise, the composition concentrations disclosed herein are given on a dry (i.e., substantially water-free) weight basis of the total weight of the components (wt. %). The dry weight for the determination of the concentration includes the weight of the acid-stable, water-soluble polyvinyl alcohol polymer, the oxidizable organic material, the chelating agent, the free radical scavenger, and any optional secondary additives, but excludes the weight of any bulk solvents (e.g., water).

Acid-Stable, Water-Soluble Polyvinyl Alcohol Polymer

The preferred water-soluble film-forming polymer of the disclosure is either a PVOH copolymer resin which is a hydrolyzed copolymer of vinyl acetate and a monomer unit having acid-stable functional groups, or a PVOH polymer modified post-polymerization by a reagent having acid-stable functional groups. The acid-stable functional groups have the function of imparting cold water solubility to the PVOH polymer, and they have the property that the imparted water-solubility is substantially unaffected by whether the acid-stable functional groups are in their native form or in a derivative form (e.g., in an acid form or in an alkali metal salt form). This property of the acid-stable functional groups contributes to the ability of the resulting PVOH polymer to remain water-soluble after prolonged exposure to an acidic environment. The preferred water-soluble, film-forming polymer is soluble in cold water (e.g., about 5° C. to about 30° C., for example about 10° C.).

The PVOH polymer preferably has a degree of hydrolysis, expressed as a percentage of vinyl acetate units converted to vinyl alcohol units, of at least 90%, and more preferably of at least about 94%.

The acid-stable, water-soluble PVOH polymer has a 4% aqueous solution viscosity at 20° C. preferably in a range of about 5 cP to about 40 cP, and more preferably in a range of about 10 cP to about 20 cP.

Suitable acid-stable functional groups include sulfonic acids (including their alkali metal salts), carboxylic acids (including their alkali metal salts), amino groups, amido groups, and cationic nitrogen groups. The PVOH polymer may include more than one type of acid-stable functional group. Preferred acid-stable functional groups are sulfonic acids and alkali metal sulfonates.

The acid-stable functional groups may be integrated into a PVOH copolymer by copolymerization of vinyl acetate with a vinyl comonomer containing one or more of the acid-stable functional groups. Examples of suitable comonomers include allylsulfonic acid, vinylsulfonic acid, ethylene sulfonic acid, 2-acrylamido-2-methylpropanesulfonic acid (SAMPS), 2-methylacrylamido-2-methylpropanesulfonic acid, maleic acid, itaconic acid, vinyl acetic acid, acrylic acid, methacrylic acid, allylamine, N-vinylformamide, vinyl pyridine, and dimethylaminoethyl vinyl ether.

Alternatively, the acid-stable functional groups may be inserted into an existing PVOH chain with a post-polymerization acetalization or other reaction such as esterification or etherification. Acetalization reactions are preferred. Examples of suitable reagents for imparting post-polymerization sulfonic acid or sulfonate functionality via acetalization include benzaldehyde 2-sulfonic acid, benzaldehyde-2,4-disulfonic acid and their sodium salts.

As used herein, the term "polyvinyl alcohol substituted with a stabilizing functional group" refers to a polymer which is the result of any suitable process for imparting additional functionality to the PVOH polymer chain, including either of the two methods described above. Specifically, it encompasses a polymer produced by either the copolymerization of vinyl acetate with an appropriate vinyl comonomer or the post-polymerization derivatization of the PVOH polymer chain, or a combination thereof.

Regardless of how conferred, the preferred level of incorporation of the acid-stable functional group-containing chemical in the PVOH polymer is preferably in a range of about 1 mol. % to about 20 mol. %, and more preferably in a range of about 2.5 mol. % to about 10 mol. %, relative to the total number of monomer units in the polymer chains. The particular level of incorporation depends on the acid-stable functional group (e.g., sulfonic acid, carboxylic acid, etc.) itself and the molecular structure attaching the functional group to the PVOH polymer chain. Specifically, the level of incorporation is preferably selected to impart cold-water solubility to the final film (which results from relatively higher levels of incorporation) while maintaining the structural and mechanical properties of the base PVOH polymer (which results from relatively lower levels of incorporation). The final film preferably is cold-water soluble such that a 75 μm film formed from the acid-stable PVOH polymer has an initial disintegration time (i.e., prior to any extended storage and/or contact with a halogenated composition) of less than about 30 seconds when measured at 10° C., and more preferably less than about 20 seconds. For example, the preferred level of incorporation is about 4 mol. % when the acid-stable functional group-containing chemical is SAMPS as a comonomer, about 8 mol. % when the acid-stable functional group-containing chemical is the acetalizing reagent benzaldehyde 2-sulfonic acid sodium salt, and about 5 mol. % when the acid-stable functional group-containing chemical is itaconic acid as a comonomer.

The concentration of the acid-stable, water-soluble PVOH polymer in the composition is preferably at least about 50 wt. %, and more preferably at least about 60 wt. %. The concentration of the acid-stable, water-soluble PVOH polymer is preferably not more than about 80 wt. %, and more preferably not more than about 75 wt. %. Alternatively, the concentration of the acid-stable, water-soluble PVOH polymer is preferably in a range of about 60 wt. % to about 75 wt. %.

Oxidizable Organic Material

Because the acid-stable, water-soluble PVOH polymer is susceptible to oxidation upon contacting a halogenated material with free halogen present (i.e., a reactive halogenated material), the halogen-resistant film-forming composition includes an oxidizable organic material that is readily and preferentially oxidized relative to the PVOH polymer. Suitable oxidizable organic materials include, but are not limited to, polyethers such as polyethylene glycol ("PEG"), PEG derivatives (e.g., methoxypolyethylene glycol ("MPEG")), polypropylene glycol ("PPG"), reducing sugars such as glucose, fructose, maltose and glyceraldehyde, and combinations of the foregoing. Preferred oxidizable organic materials are polyethylene glycols, more preferred are polyethylene glycols that are solid at room temperature (e.g., PEG having a molecular weight of at least about 900 Daltons, MPEG having a molecular weight of at least about 750 Daltons, and mixtures thereof), and particularly preferred is PEG having a molecular weight of about 3350 Daltons.

The concentration of the oxidizable organic material is preferably at least about 2 wt. %, and more preferably at least about 3 wt. %. The concentration of the oxidizable organic material is preferably not more than about 20 wt. %, and more preferably not more than about 10 wt. %. Contemplated ranges for the oxidizable organic material concentration include about 2 wt. % to about 10 wt. %, for example about 5 wt. %.

Chelating Agent

Because the oxidation of the PVOH polymer can be catalyzed by trace metal ions, the halogen-resistant film-forming composition includes a chlorine-stable chelating agent to bind free metal ions and thereby inhibit catalysis by the free metal ions. Suitable chelating agents include, but are not limited to, phosphonic acids, phosphonates, polyphosphates, polyaminocarboxylic acids (e.g., EDTA (ethylenediamine tetraacetic acid), DTPA (diethylenetriamine pentaacetic acid), and NTA (nitrilotriacetic acid)), and mixtures thereof. A preferred chelating agent is 1-hydroxyethylidene-1,1-phosphonic acid, which is commercially available as a 60 wt. % aqueous solution under the name DEQUEST 2010 (available from Solutia, Inc. of St. Louis, Mo.).

The concentration of the chelating agent is preferably at least about 0.05 wt. %, and more preferably at least about 0.07 wt. %. The concentration of the chelating agent is preferably not more than about 0.2 wt. %, and more preferably not more than about 0.15 wt. %. Contemplated ranges for the chelating agent concentration include about 0.05 wt. % to about 0.2 wt. %, and about 0.07 wt. % to about 0.15 wt. %, for example about 0.1 wt. %.

Free Radical Scavenger

Without intending to be limited by any particular theory, it is believed that the mechanism of PVOH oxidation involves reactive free radicals, including chlorine free radicals, which abstract hydrogen atoms from PVOH hydroxyl groups. It is believed that carbonyl groups are so formed on the polymer backbone as well as intermolecular crosslinks among polymer chains. Therefore, the halogen-resistant film-forming composition optionally includes a free radical scavenger to preferentially react with the free radicals, thereby inhibiting these reactions. Suitable free radical scavengers include, but are not limited to, 4-methoxy phenol ("MEHQ"), hydroquinone, ascorbic acid, butylated hydroxyanisole ("BHA"), thiols (e.g., mercaptopropionic acid and N-acetylcysteine), dimethylthiourea, pyrrolidine dithiocarbamate, hydroxylamines, monoterpene ketones, and mixtures thereof. A preferred free radical scavenger is MEHQ.

The concentration of the free radical scavenger is preferably at least about 0.1 wt. %, and more preferably at least about 1 wt. %. The concentration of the free radical scavenger is preferably not more than about 5 wt. %, and more preferably not more than about 4 wt. %. Contemplated ranges for the free-radical scavenger concentration include about 0.1 wt. % to about 5 wt. %, and about 1 wt. % to about 4 wt. %, for example about 3 wt. %.

Additives

The halogen-resistant film-forming composition can optionally include secondary additives such as plasticizers, lubricants, and surfactants. Convenient surfactants, representing additional readily oxidizable organic materials, are polyoxyethylene sorbitan fatty acid esters (e.g., TWEEN surfactancts) and ethylene oxide-propylene oxide block copolymers (e.g., PLURONIC surfactants). One or more secondary additives can be included at any concentrations that do not materially affect the water solubility and preferably also the physical integrity of the structure (e.g., film) resulting from the composition. Concentrations typically known and used in the art of water soluble films, especially water-soluble packaging films, are contemplated for use.

Halogen-Resistant Film-Forming Composition

A halogen-resistant film preferably is prepared by the solution casting of an aqueous mixture (e.g., solution) of the acid-stable, water-soluble polyvinyl alcohol polymer, oxidizable organic material, chelating agent, free radical scavenger, and any secondary additives. The resulting film can have any suitable thickness, for example in a range of about 40 µm to about 50 µm.

The process of forming, filling, and sealing a package made from a film is generally known in the art. During one type of packaging process, the halogen-resistant film is shaped into a package, the package is filled with a reactive halogen-containing composition such that the halogen-containing composition is in direct contact with the film, and then the package is heat sealed. Example reactive halogen-containing compositions include water treatment products containing compounds such as trichloroisocyanuric acid, dichloroisocyanuric acid, and their sodium and potassium salts, sodium hypochlorite, calcium hypochlorite, N,N-dichlorohydantoin, N,N-dibromohydantoin, and N-chloro-N-bromo-5,5-dimethylhydantoin. Once in this form, the film package containing the halogenated composition can be stored over a period of at least several months under variable climatic conditions without an appreciable loss of its water-soluble character.

Conventional water-soluble films made from polyvinyl alcohol can have limitations when used to form packages for reactive halogenated chemicals, for example in that the halogenated chemicals can discolor and limit the solubility of the film after prolonged exposure. For instance, free chlorine and bromine can oxidize the PVOH, rendering it insoluble and causing it to become discolored. Similarly, when the water solubility of the film is imparted by a partially hydrolyzed PVOH homopolymer, the acidic environment created by the halogenated package contents (e.g., hydrochloric acid and hypochlorous acid) can increase the level of hydrolysis of the PVOH homopolymers, thereby limiting it to hot water solubility. Without intending to be limited by any particular theory, it is also believed that PVOH films can become more water insoluble as a result of the formation of intermolecular crosslinks induced by the abstraction of a hydrogen atom from a hydroxyl group in the presence of reactive radicals in the halogenated package contents.

The compositions described herein are useful as halogen-resistant, water-soluble articles, including films that can be used to package ingredients such as water treatment products. In one class of embodiments, a film formed from the composition is characterized by a relatively small increase in disintegration and/or dissolution time in water (i.e., the relative change in disintegration and/or dissolution time between the initial and final states after contact with a reactive halogenated compound for a prescribed amount of time).

The halogen-resistant, film-forming composition is preferably characterized by an increase in dissolution time of not more than 50%, more preferably not more than 15%, and most preferably not more than 10%, when a 50 µm film formed from the composition is stored in contact with a reactive halogenated composition including 56 wt. % sodium dichloroisocyanurate as the active ingredient for 28 days at 38° C. and 85% relative humidity and then measured in water at 10° C. In the same or an alternative embodiment, the 50 µm film stored and measured under these conditions has an absolute dissolution time of preferably not more than about 90 seconds, more preferably not more than about 60 seconds, and most preferably not more than about 30 seconds, for example about 27 seconds.

The halogen-resistant, film-forming composition is preferably characterized by an increase in disintegration time of not more than 50%, and more preferably not more than 30%, when a 50 µm film formed from the composition is stored in contact with a reactive halogenated composition including 56 wt. % sodium dichloroisocyanurate as the active ingredient for 28 days at 38° C. and 85% relative humidity and then measured in water at 10° C. In the same or an alternative embodiment, the 50 µm film stored and measured under these conditions has an absolute disintegration time of preferably not more than about 60 seconds, more preferably not more than about 30 seconds, and most preferably not more than about 15 seconds, for example about 14 seconds.

The halogen-resistant, film-forming composition is preferably characterized by an increase in dissolution time of not more than 50%, more preferably not more than 15%, and most preferably not more than 10%, when a 50 µm film formed from the composition is stored in contact with a reactive halogenated composition including 56 wt. % sodium dichloroisocyanurate as the active ingredient for 28 days at 38° C. and 10% relative humidity and then measured in water at 10° C. In the same or an alternative embodiment, the 50 μm film stored and measured under these conditions has an absolute dissolution time of preferably not more than about 90 seconds, more preferably not more than about 60 seconds, and most preferably not more than about 30 seconds, for example about 29 seconds.

The halogen-resistant, film-forming composition is preferably characterized by an increase in disintegration time of not more than 50%, more preferably not more than 15%, and most preferably not more than 10%, when a 50 μm film formed from the composition is stored in contact with a reactive halogenated composition including 56 wt. % sodium dichloroisocyanurate as the active ingredient for 28 days at 38° C. and 10% relative humidity and then measured in water at 10° C. In the same or an alternative embodiment, the 50 μm film stored and measured under these conditions has an absolute disintegration time of preferably not more than about 60 seconds, more preferably not more than about 30 seconds, and most preferably not more than about 15 seconds, for example about 12 seconds.

The halogen-resistant, film-forming composition is preferably characterized by an increase in dissolution time of not more than 50%, and more preferably not more than 30%, when a 50 μm film formed from the composition is stored in contact with a reactive halogenated composition including 56 wt. % sodium dichloroisocyanurate as the active ingredient for 28 days at 23° C. and 50% relative humidity and then measured in water at 10° C. In the same or an alternate embodiment, the 50 μm film stored and measured under these conditions has an absolute dissolution time of preferably not more than about 90 seconds, more preferably not more than about 60 seconds, and most preferably not more than about 35 seconds, for example about 34 seconds.

The halogen-resistant, film-forming composition is preferably characterized by an increase in disintegration time of not more than 50%, more preferably not more than 15%, and most preferably not more than 10%, when a 50 μm film formed from the composition is stored in contact with a reactive halogenated composition including 56 wt. % sodium dichloroisocyanurate as the active ingredient for 28 days at 23° C. and 50% relative humidity and then measured in water at 10° C. In the same or an alternate embodiment, the 50 μm film stored and measured under these conditions has an absolute disintegration time of preferably not more than about 60 seconds, more preferably not more than about 30 seconds, and most preferably not more than about 15 seconds, for example about 9 seconds.

Various embodiments of the halogen-resistant film-forming composition described herein can optionally yield one or more advantages. For example, the composition described herein can provide a film which is convenient to shape and fill with a water treatment product. Suitable water treatment products include swimming pool and spa sanitizing chemicals containing halogens, in particular chlorine and bromine. Once formed into a package containing the halogenated compositions, a film can be designed to retain its water soluble character over extended periods and under variable climatic conditions.

Method for the Determination of Film Water Solubility

Figure 1:
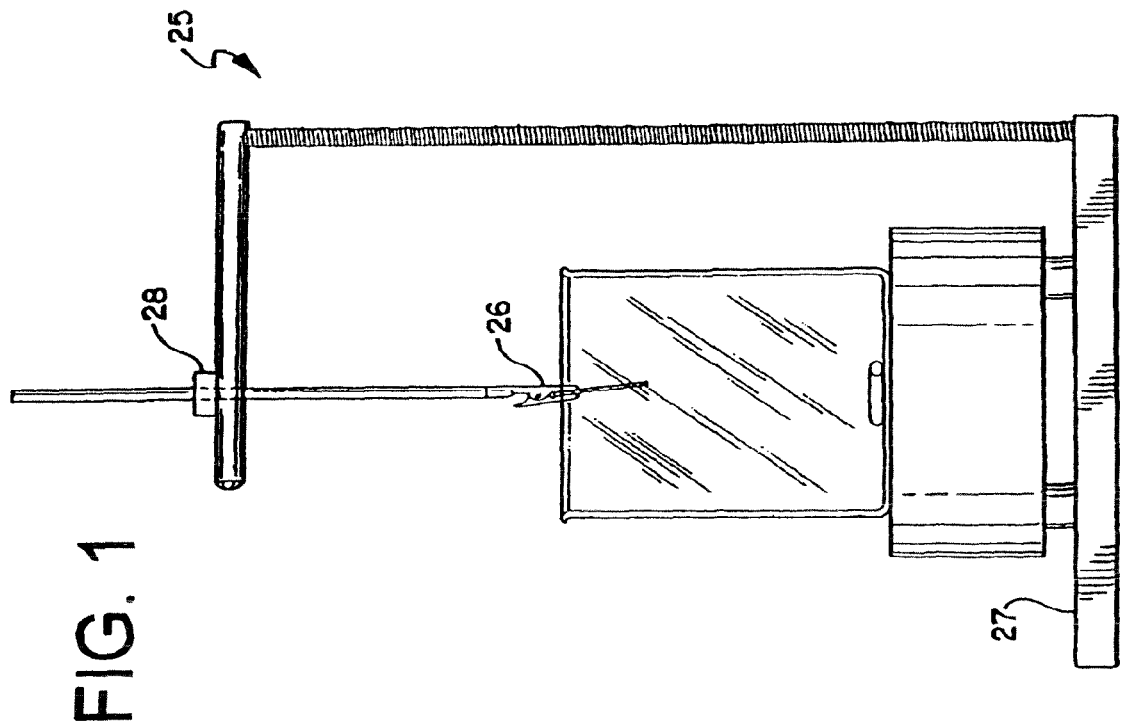
FIG. 1 is a perspective view of a test apparatus used to determine the water disintegration and water dissolution times of film test samples.
Figure 2:
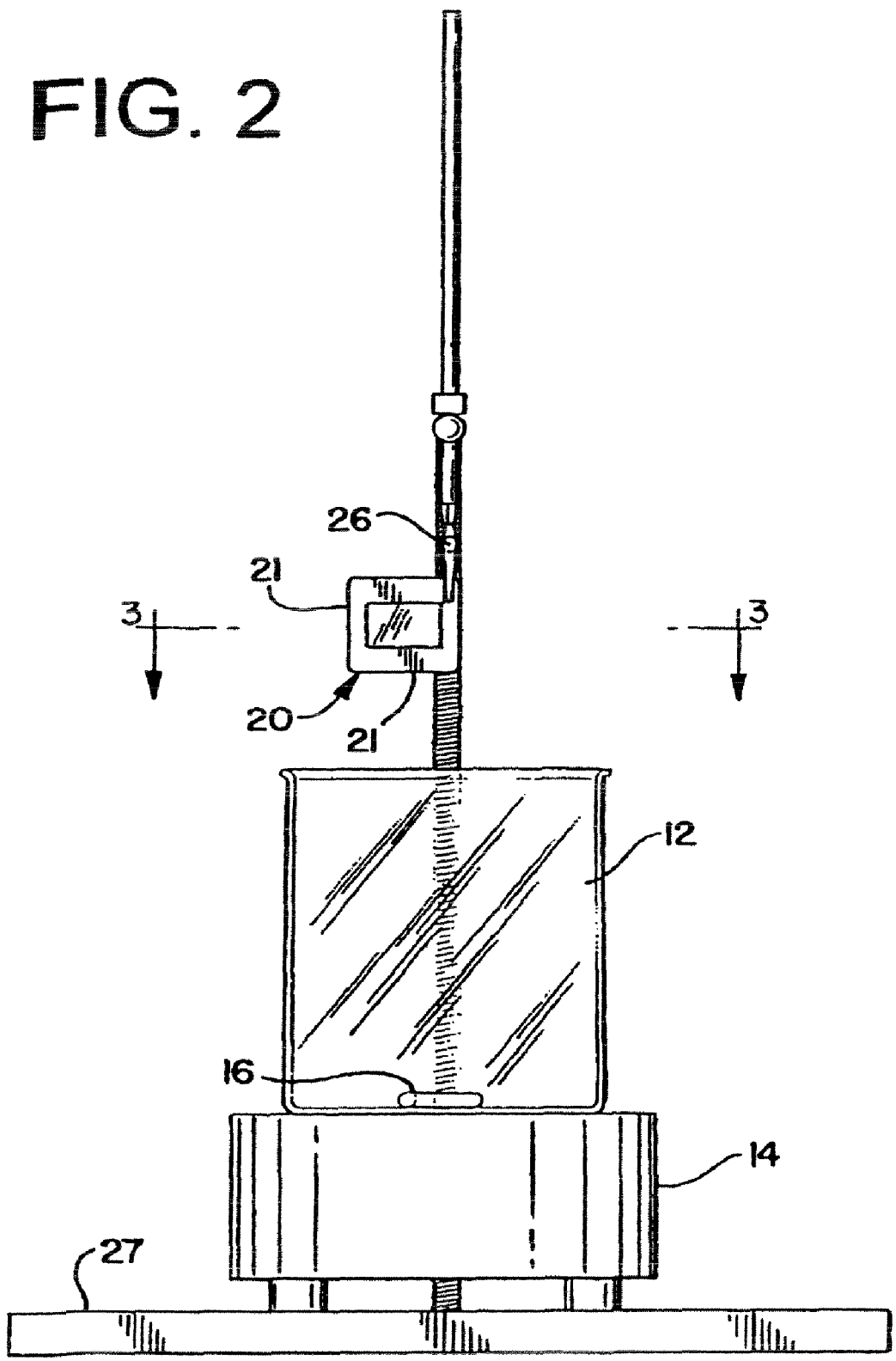
FIG. 2 is a perspective view of the test apparatus and test set-up illustrating the procedure for determining the water-solubility of film test samples; and, FIG. 3 is a top view of the test set-up of FIG. 2.

The following test procedure describes, with reference to FIGS. 1-3, an objective method for characterizing the water-solubility of a film test sample. The method involves the determination of the disintegration and dissolution times of the film test sample prior to and after prolonged contact with a halogenated composition. As used herein, the terms "increase in disintegration time" and "increase in dissolution time" indicate the relative change in disintegration/dissolution time when comparing the disintegration/dissolution time after some prescribed storage duration (e.g., 28 days under specified climatic conditions with the test film in contact with a halogenated composition) to the disintegration/dissolution time prior to storage and contact with a halogenated composition.

Apparatus and Materials 600 mL Beaker 12

Magnetic Stirrer 14 (Labline Model No. 1250 or equivalent)

Magnetic Stirring Rod 16 (5 cm)

Thermometer (0° C. to 100° C., ±1° C.)

Template, Stainless Steel (3.8 cm×3.2 cm)

Timer, (up to 300 seconds, accurate to the nearest second)

Polaroid 35 mm Slide Mount 20 (or equivalent)

MonoSol 35 mm Slide Mount Holder 25 (or equivalent, see FIG. 1)

Distilled Water

Test Procedure

1. Cut three test specimens from a film sample of known thickness (e.g., 50 μm) using stainless steel template (i.e., 3.8 cm×3.2 cm specimen). If cut from a film web, specimens should be cut from areas of web evenly spaced along the transverse direction of the web.
2. Lock each specimen in a separate 35 mm slide mount 20.
3. Fill beaker 12 with 500 mL of distilled water. Measure water temperature with thermometer and, if necessary, heat or cool water to maintain a constant temperature (e.g., 10° C./50° F.).
4. Mark height of column of water. Place magnetic stirrer 14 on base 27 of holder 25. Place beaker 12 on magnetic stirrer 14, add magnetic stirring rod 16 to beaker 12, turn on stirrer 14, and adjust stir speed until a vortex develops which is approximately one-fifth the height of the water column. Mark depth of vortex.
5. Secure the 35 mm slide mount 20 in the alligator clamp 26 of the MonoSol 35 mm slide mount holder 25 (FIG. 1) such that the long end 21 of the slide mount 20 is parallel to the water surface, as illustrated in FIG. 2. The depth adjuster 28 of the holder 25 should be set so that when dropped, the end of the clamp 26 will be 0.6 cm below the surface of the water. One of the short sides 23 of the slide mount 20 should be next to the side of the beaker 12 with the other positioned directly over the center of the stirring rod 16 such that the film surface is perpendicular to the flow of the water, as illustrated in FIG. 3.
6. In one motion, drop the secured slide and clamp into the water and start the timer. The disintegration time is noted when the film breaks apart. When all visible film is released from the slide mount, raise the slide out of the water while continuing to monitor the solution for undissolved film fragments. The dissolution time is noted when all film fragments are no longer visible and the solution becomes clear.

The results from this test procedure should include: a complete film test sample identification, the film characteristics (e.g., chemical components, film thickness, etc.), the storage conditions of the film (e.g., time, temperature, relative humidity, package contents, etc.), the point in the storage history at which the test was performed (e.g., initial test, test after 28 days of storage, etc.), and the water temperature at which the samples were tested. The test specifies that three samples are tested and averaged, although more replicates may be performed for each set of test conditions for increased accuracy and precision, and statistical analyses may be incorporated (i.e., beyond the average).

The following examples, in which film compositions were prepared and tested to measure their ability to remain water soluble after prolonged exposure to a halogenated composition, are provided for illustration and are not intended to limit the scope of the invention. The films were prepared by blending the various components and then performing a conventional solution casting process to create a film having a thickness of about 40 μm to 50 μm, and were not conditioned after casting. The films were then formed into packages.

EXAMPLE 1

A 50 μm film was prepared by solution casting, and contained an acid-stable, water-soluble polyvinyl alcohol copolymer, an oxidizable organic material, a chelating agent, a free radical scavenger, and secondary additives unrelated to solubility. The specific copolymer was a PVOH-SAMPS copolymer having a 4% solution viscosity at 20° C. of 11.6 cP, a level of incorporation of SAMPS of 4.0 mol. % and a degree of hydrolysis of 95.5%. A package made from the film was filled with 50 g of a 56 wt. %-active sodium dichloroisocyanurate pool sanitizer, sealed, and then stored for 28 days under various climatic conditions (i.e., temperature and relative humidity; see Table 1). After 28 days and under all tested conditions, the film retained its original color.

COMPARATIVE EXAMPLE 1

A 50 μm film representative of conventional water-soluble films was prepared by solution casting using a PVOH homopolymer having a 4% solution viscosity at 20° C. of 23 cP and a degree of hydrolysis of 88%. A package made from the film was filled with 50 g of a 56 wt. %-active sodium dichloroisocyanurate pool sanitizer, sealed, and then stored for 28 days under various climatic conditions (i.e., temperature and relative humidity; see Table 1). After 28 days and under all tested conditions, the film had become a brownish yellow color.

COMPARATIVE EXAMPLE 2

Another conventional, 40 μm water-soluble film was prepared by solution casting using an acid-stable, water-soluble polyvinyl alcohol copolymer, a water solubility additive, and a reducing hydroxycarboxylic acid. The specific copolymer was a PVOH-SAMPS copolymer having a 4% solution viscosity at 20° C. of 11.6 cP, a level of incorporation of SAMPS of 4.0 mol. %, and a degree of hydrolysis of 95.5%. Trichloroisocyanuric acid (available as a 3"-diameter tablet form under the name MAXI-CHLOR, from N. Jonas & Co., Bensalem, Pa.), was wrapped in the film, sealed, and then stored for 28 days under various climatic conditions (i.e., temperature and relative humidity; see Table 1). After 28 days and under all tested conditions, the film was essentially insolubilized, although it retained its original color.

The components, amounts, and solubility characteristics for each example are given in Table 1. For each of the water solubility entries, the first number is the disintegration time in 10° C. water, and the second number is the dissolution time in 10° C. water, as determined by the method described above. The first solubility entry represents the film prior to exposure to a halogenated composition. For the solubility entries after 28 days of storage and exposure, the results are listed as a function of storage temperature (° C.) and relative humidity (%). The entry "Insol." indicates that the sample either did not disintegrate or dissolve within 300 seconds, respectively. In the case of Comparative Example 2 and after prolonged exposure to the halogenated composition, small insoluble pieces of film remained after 300 seconds, despite that the film retained its ability to disintegrate in cold water.

TABLE 1

| | Component | | | Water Solubility at 10° C. | | | |
|---|---|---|---|---|---|---|---|
| Sample | Name (wt. %) | Function | Initial | 28d @ 23° C./ 50% RH | 28d @ 23° C./ 80% RH | 28d @ 38° C./ 10% RH | 28d @ 38° C./ 85% RH |
| Example 1 | PVOH-SAMPS (71.8) | Acid-stable Copolymer | 11 sec 27 sec | 9 sec 34 sec | N/A N/A | 12 sec 29 sec | 14 sec 27 sec |
| | Polyethylene glycol, MW 3350 (5.0) | Oxidizable Organic Material | | | | | |
| | 1-Hydroxyethylidene-1,1-phosphonic acid (0.1) | Chelating Agent | | | | | |
| | 4-Methoxy phenol (2.9) | Free Radical Scavenger | | | | | |
| | Secondary additives (20.2) | | | | | | |
| Comparative Example 1 | PVOH (73.5) | Conventional Homopolymer | 20 sec 41 sec | Insol. Insol. | N/A N/A | Insol. Insol. | Insol. Insol. |
| | Secondary additives (26.5) | | | | | | |
| Comparative Example 2 | PVOH-SAMPS (70.8) | Acid-stable Copolymer | 9 sec 20 sec | 10 sec Insol. | 13 sec Insol. | N/A N/A | N/A N/A |
| | Propyl gallate (1.4) | Water Solubility Additive | | | | | |
| | Citric acid (0.7) | Reducing Hydroxycarboxylic Acid | | | | | |
| | Secondary additives (27.1) | | | | | | |

The foregoing description is given for clearness of understanding only, and no unnecessary limitations should be understood therefrom, as modifications within the scope of the invention may be apparent to those having ordinary skill in the art.

Throughout the specification, where the composition is described as including components or materials, it is contemplated that the compositions can also consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A halogen-resistant film composition, comprising: a mixture of
   an acid-stable, water-soluble polyvinyl alcohol polymer;
   an oxidizable organic material;
   a chelating agent selected from the group consisting of phosphonic acids, phosphonates, polyphosphates, polyaminocarboxylic acids, and combinations thereof; and
   a free radical scavenger;
   wherein the mixture is in the form of a water-soluble film.

2. The halogen-resistant film composition of claim 1, wherein the free radical scavenger is selected from the group consisting of 4-methoxy phenol, hydroquinone, ascorbic acid, butylated hydroxyanisole, mercaptopropionic acid, N-acetylcysteine, dimethylthiourea, pyrrolidine dithiocarbamate, hydroxylamines, monoterpene ketones, and combinations thereof.

3. The halogen-resistant film composition of claim 1, wherein the free radical scavenger is present in a range of about 0.1 wt. % to about 5 wt. %, on a dry weight basis of the total weight of the composition.

4. The halogen-resistant film composition of claim 1, characterized by an increase in dissolution time of not more than 50 % for a 50 μm film composition stored in contact with a reactive halogenated composition including 56 wt. % sodium dichloroisocyanurate as the active ingredient for 28 days at 38° C. and 85 % relative humidity and then measured in water at 10° C.

5. The halogen-resistant film composition of claim 4, wherein the increase in dissolution time is not more than 15%.

6. The halogen-resistant film composition of claim 1, characterized by an increase in disintegration time of not more than 50% for a 50 μm film composition stored in contact with a reactive halogenated composition including 56 wt. % sodium dichloroisocyanurate as the active ingredient for 28 days at 38° C. and 85% relative humidity and then measured in water at 10° C.

7. The halogen-resistant film composition of claim 1, wherein the acid-stable, water-soluble polyvinyl alcohol polymer comprises polyvinyl alcohol substituted with a stabilizing functional group selected from the group consisting of sulfonic acid, sulfonic acid alkali metal salts; carboxylic acid, carboxylic acid alkali metal salts; amine; amide; cationic nitrogen; and, combinations thereof.

8. The halogen-resistant film composition of claim 7, wherein the level of incorporation of the stabilizing functional group in the acid-stable, water-soluble polyvinyl alcohol polymer is in a range of about 1 mol. % to about 20 mol. %, relative to the total number of monomer units in the polymer chains.

9. The halogen-resistant film composition of claim 8, wherein the level of incorporation of the stabilizing functional group in the acid-stable, water-soluble polyvinyl alcohol polymer is in a range of about 2.5 mol. % to about 10 mol. %, relative to the total number of monomer units in the polymer chains.

10. The halogen-resistant film composition of claim 1, wherein the oxidizable organic material is selected from the group consisting of polyethylene glycol, derivatives of polyethylene glycol, polypropylene glycol, reducing sugars, glucose, fructose, maltose, glyceraldehyde, and combinations thereof.

11. The halogen-resistant film composition of claim 10, wherein the oxidizable organic material is selected from the group consisting of polyethylene glycol having a molecular weight of at least about 750 Daltons and a solid consistency at room temperature, polyethylene glycol derivatives having a molecular weight of at least about 750 Daltons and a solid consistency at room temperature, and combinations thereof.

12. The halogen-resistant film composition of claim 1, wherein
   the acid-stable, water-soluble polyvinyl alcohol polymer is present in a range of about 60 wt. % to about 75 wt. %, on a dry weight basis of the total weight of the composition;
   the oxidizable organic material is present in a range of about 2 wt. % to about 20 wt. %, on a dry weight basis of the total weight of the composition; and
   the chelating agent is present in a range of about 0.05 wt. % to about 0.2 wt. %, on a dry weight basis of the total weight of the composition.

13. The halogen-resistant film composition of claim 1, wherein the acid-stable, water-soluble polyvinyl alcohol polymer has a 4% solution viscosity at 20° C. in a range of about 5 cP to about 40 cP.

14. The halogen-resistant film composition of claim 13, wherein the acid-stable, water-soluble polyvinyl alcohol polymer has a 4% solution viscosity at 20° C. in a range of about 10 cP to about 20 cP.

15. The halogen-resistant film composition of claim 1, wherein the degree of hydrolysis of the acid-stable, water-soluble polyvinyl alcohol polymer, expressed as a percentage of vinyl acetate units converted to vinyl alcohol units, is at least about 90%.

16. The halogen-resistant film composition of claim 1, further comprising a secondary additive selected from the group consisting of plasticizers, lubricants, surfactants, and combinations thereof.

17. A pre-packaged sanitizing article, comprising: a reactive halogenated component contained in and in contact with a water-soluble film package formed from the halogen-resistant film composition of claim 1.

18. A halogen-resistant composition, comprising: a water-soluble film, the water-soluble film comprising a mixture of
   an acid-stable, water-soluble polyvinyl alcohol polymer;
   an oxidizable organic material,
   a chelating agent selected from the group consisting of phosphonic acids, phosphonates, polyphosphates, polyaminocarboxylic acids, and combinations thereof, and
   a free radical scavenger;
   wherein the water-soluble film is characterized by an increase in dissolution time of not more than 15% for a 50 μm film stored in contact with a reactive halogenated composition including 56 wt. % sodium dichloroisocyanurate as the active ingredient for 28 days at 38° C. and 85% relative humidity and then measured in water at 10° C.

19. The halogen-resistant composition of claim 18, wherein the increase in dissolution time is not more than 10%.

20. The halogen-resistant composition of claim 18, wherein the water-soluble film is characterized by an increase in disintegration time of not more than 50% for a 50 µm film stored in contact with a reactive halogenated composition including 56 wt. % sodium dichloroisocyanurate as the active ingredient for 28 days at 38° C. and 85% relative humidity and then measured in water at 10° C.

21. A halogen-resistant film composition, comprising: a mixture of
 an acid-stable, water-soluble polymer comprising polyvinyl alcohol substituted with a stabilizing functional group selected from the group consisting of sulfonic acid, sulfonic acid alkali metal salts; carboxylic acid, carboxylic acid alkali metal salts; amine; amide; cationic nitrogen; and, combinations thereof;
 an oxidizable organic material selected from the group consisting of polyethylene glycol, methoxypolyethyleneglycol, polypropylene glycol, reducing sugars, glucose, fructose, maltose, glyceraldehyde, and combinations thereof;
 a chelating agent selected from the group consisting of phosphonic acids, phosphonates, polyphosphates, polyaminocarboxylic acids, and combinations thereof; and
 a free radical scavenger selected from the group consisting of 4-methoxy phenol, hydroquinone, ascorbic acid, butylated hydroxyanisole, mercaptopropionic acid, N-acetylcysteine, dimethylthiourea, pyrrolidine dithiocarbamate, hydroxylamines, monoterpene ketones, and combinations thereof:
wherein the mixture is in the faun of a water-soluble film.

22. The halogen-resistant film composition of claim 21, wherein:
 the acid-stable, water-soluble polymer is present in a range of about 60 wt. % to about 75 wt. %, on a dry weight basis of the total weight of the composition;
 the oxidizable organic material is present in a range of about 2 wt. % to about 20 wt. %, on a dry weight basis of the total weight of the composition;
 the chelating agent is present in a range of about 0.05 wt. % to about 0.2 wt. %, on a dry weight basis of the total weight of the composition; and
 the free radical scavenger is present in a range of about 0.1 wt. % to about 5 wt. %, on a dry weight basis of the total weight of the composition.

23. The halogen-resistant film composition of claim 21, wherein:
 the acid-stable, water-soluble polymer comprises a hydrolyzed copolymer of vinyl acetate and a comonomer selected from the group consisting of 2-acrylamido-2-methylpropanesulfonic acid, alkali metal salts thereof, and combinations thereof;
 the oxidizable organic material comprises polyethylene glycol having a molecular weight of about 3350 Daltons;
 the chelating agent comprises 1-hydroxyethylidene-1,1-phosphonic acid; and
 the free radical scavenger comprises 4-methoxy phenol.

24. The halogen-resistant film composition of claim 21, wherein:
 the acid-stable water-soluble polymer comprises a polyvinyl alcohol polymer modified post-polymerization by acetalization with a member selected from the group consisting of benzaldehyde-2-sulfonic acid, benzaldehyde-2-sulfonic acid alkali metal salts, and combinations thereof;
 the oxidizable organic material comprises polyethylene glycol having a molecular weight of about 3350 Daltons;
 the chelating agent comprises 1-hydroxyethylidene-1,1-phosphonic acid; and, the free radical scavenger comprises 4-methoxy phenol.

25. The halogen-resistant film composition of claim 21, wherein the water-soluble film is in the form of a package.

* * * * *

UNITED STATES PATENT AND TRADEMARK OFFICE
CERTIFICATE OF CORRECTION

| | | |
|---|---|---|
| PATENT NO. | : 7,803,872 B2 | Page 1 of 1 |
| APPLICATION NO. | : 11/739473 | |
| DATED | : September 28, 2010 | |
| INVENTOR(S) | : Andrew P. Verrall et al. | |

It is certified that error appears in the above-identified patent and that said Letters Patent is hereby corrected as shown below:

In the Claims

At Column 13, Line 31, "faun" should be -- form --.

Signed and Sealed this
Thirty-first Day of January, 2023

Katherine Kelly Vidal
Director of the United States Patent and Trademark Office